United States Patent [19]
Doan

[11] Patent Number: 5,247,344
[45] Date of Patent: Sep. 21, 1993

[54] OPTICAL INSPECTION SYSTEM FOR SOLDER JOINTS AND INSPECTION METHOD

[75] Inventor: Tam D. Doan, Orange, Calif.

[73] Assignee: Hughes Aircraft Company, Los Angeles, Calif.

[21] Appl. No.: 678,161

[22] Filed: Mar. 28, 1991

Related U.S. Application Data

[63] Continuation of Ser. No. 252,476, Oct. 3, 1988, abandoned.

[51] Int. Cl.[5] .................. G01B 11/00; H04N 7/00
[52] U.S. Cl. ............................ 356/394; 358/101; 358/106; 358/107; 356/237
[58] Field of Search ............ 356/394, 237, 376, 398; 250/572; 358/101, 106, 107; 382/8, 22

[56] References Cited

U.S. PATENT DOCUMENTS

| | | | |
|---|---|---|---|
| 4,028,728 | 6/1977 | Sharp | 356/237 |
| 4,595,289 | 6/1986 | Feldman et al. | 356/237 |
| 4,677,473 | 6/1987 | Okamoto et al. | 356/376 |
| 4,688,939 | 8/1987 | Ray | 356/237 |
| 4,811,410 | 3/1989 | Amir et al. | 356/237 |

FOREIGN PATENT DOCUMENTS

| | | | |
|---|---|---|---|
| 0007311 | 1/1985 | Japan | 356/376 |
| 0299709 | 12/1987 | Japan | 356/376 |

*Primary Examiner*—Richard A. Rosenberger
*Assistant Examiner*—Hoa Pham
*Attorney, Agent, or Firm*—L. A. Alkov; W. K. Denson-Low

[57] ABSTRACT

The adequacy of the fillets (24, 26) by which the lead (22) is soldered to pad (18) on printed circuit board (16) is evaluated by providing low angle diffuse illumination from circular fluorescent lamp (34) and observing the image with a television camera (30). The electronic image information is digitized and analyzed to produce a signal corresponding to the adequacy of the fillets and thus the adequacy of the solder joint. Automatic inspection is achieved and the signal can be employed to translate the printed wiring board to a new position for automatic inspection of another solder joint.

14 Claims, 3 Drawing Sheets

OPTICAL INSPECTION SYSTEM FOR SOLDER JOINTS AND INSPECTION METHOD

This is a continuation of application Ser. No. 07/252,476 filed Oct. 3, 1988, abandoned.

FIELD OF THE INVENTION

This invention is directed to a system for evaluating the quality of solder joints, by employing low-angle, diffuse illumination, video digitization of the image and processing the digitized image data to determine the nature of the inspected solder joint on the basis of its visual appearance.

BACKGROUND OF THE INVENTION

Much of modern electronic assembly is automatic. A robot with specially fabricated grasping fingers grasps a selected electronic component from a dispensing station. This component may be a flat pack with a plurality of flat leads extending from one or more sides thereof or may be a cylindrical component such as a resistor having round wire leads thereon. The leads of the components are shaped in such a manner that they lie at or below the bottom surface of the component for surface mounting on the printed wiring board. After a component is grasped, the component may be optically inspected so that it is the correct component for this particular assembly step. Next, the component may have its leads fluxed, and thereafter the component is put in place on the printed wiring board. When it is put in place, its leads are located on solder pads which have sufficient solder thereon for reflow soldering to the leads on the component. When placed, heater bars are brought over the component leads and are brought down on the leads to hold them in place. While held in place, the heater bars heat the leads and the adjacent solder to reflow solder the leads in place. The assembly is complete, except for the inspection of the adequacy of the solder joint. Present inspection is visual. The inspection is by employment of microscopes having magnification of under four times to microscopes having magnification of seven times. Prior art lighting is usual microscope illumination, about 45 degrees to the perpendicular to the surface of the printed wiring board. This is the best quality control inspection presently available, but its disadvantages include the subjectivity of the inspection and the personal judgment required. This is compounded by limited visual acuity and limited attention span. The article must be manually moved with respect to the microscope which can cause hand-eye coordination errors. Each of the errors increases with fatigue as the work day goes on. As a result of this, an accept-reject decision cannot be repeated with 100 percent repeatability. In addition, such inspection methods are labor intensive and require expensive training together with periodic certification of the trained inspectors.

There have been attempts to automatically inspect by means of laser illumination together with infra-red signature sensing and analysis technique. The problem with the infra-red inspection technique is that it cannot detect all visual defects. It is not as sensitive to problems as a good visual inspection. It cannot detect extraneous solder, away from the solder pads. It cannot detect subtle visual solder defects such as insufficient solder or dewet conditions, where the solder does not wet both surfaces of the intended solder joint. Further, it cannot detect misalignment between the leads and the pads. Other attempts at automatic inspection include the use of two colors of light at different illumination angles, but such have not been reliable to date. Thus, present-day automatic inspection has not been satisfactory.

SUMMARY OF THE INVENTION

In order to aid, in the understanding of this invention, it can be stated in essentially summary form that it is directed to an optical inspection system for solder joints and to an inspection method wherein the system comprises illuminating the solder joint with diffuse light at a low angle with respect to the surface of the printed wiring board, employing a video camera to transduce the image to electronic signals, digitizing the signals by using an image processor, and processing and analyzing the image data to determine whether or not the image of the solder joint indicates a satisfactory solder joint so that automatic solder joint inspection and evaluation of the joint is achieved.

It is thus a purpose and advantage of this invention to provide an optical inspection system which has a wide capability of solder joint inspection to observe and analyze and automatically determine the quality of a solder joint, to reliably inspect and evaluate solder joints.

It is another purpose and advantage of this invention to reduce costs by eliminating visual inspection of solder joints and to reduce machine time by quickly and accurately inspecting and evaluating solder joints.

It is another purpose and advantage of this invention to provide a system where the quality of solder joints of various components can be inspected without the involvement of machine down time for adjustment between types of solder joints.

It is another purpose and advantage of this invention to provide an optical inspection system for solder joints which removes the subjectivity and judgment, as well as the fatigue and limited visual acuity attendant upon visual inspection.

Other purposes and advantages of this invention will become apparent from a study of the following portion of the specification, the claims and the attached drawings.

DESCRIPTION OF THE PREFERRED EMBODIMENT

Figure 1:
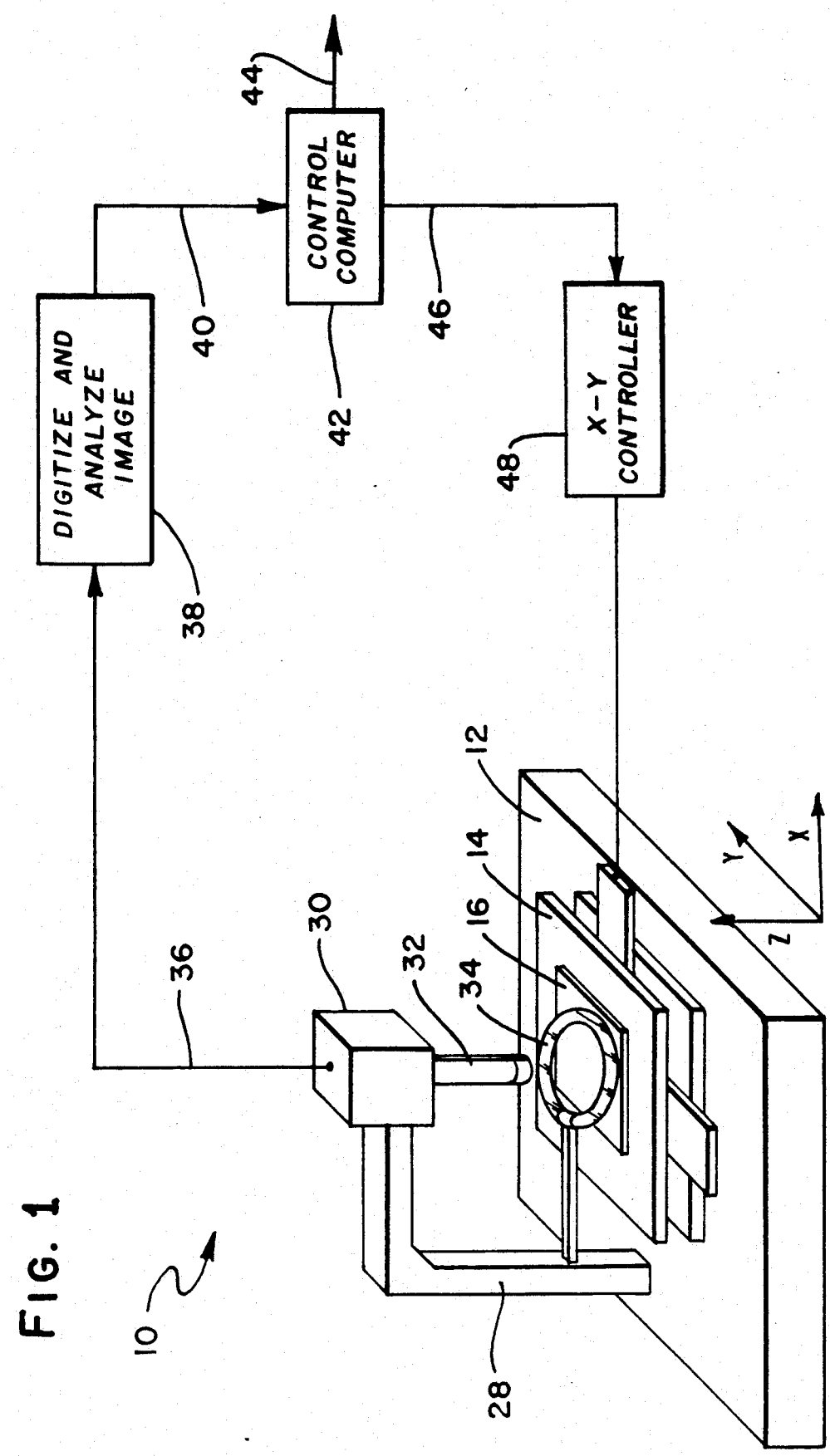
FIG. 1 is a perspective view of an inspection station having the optical inspection system of this invention therein, together with some of the system shown in block diagram.
Figure 2:
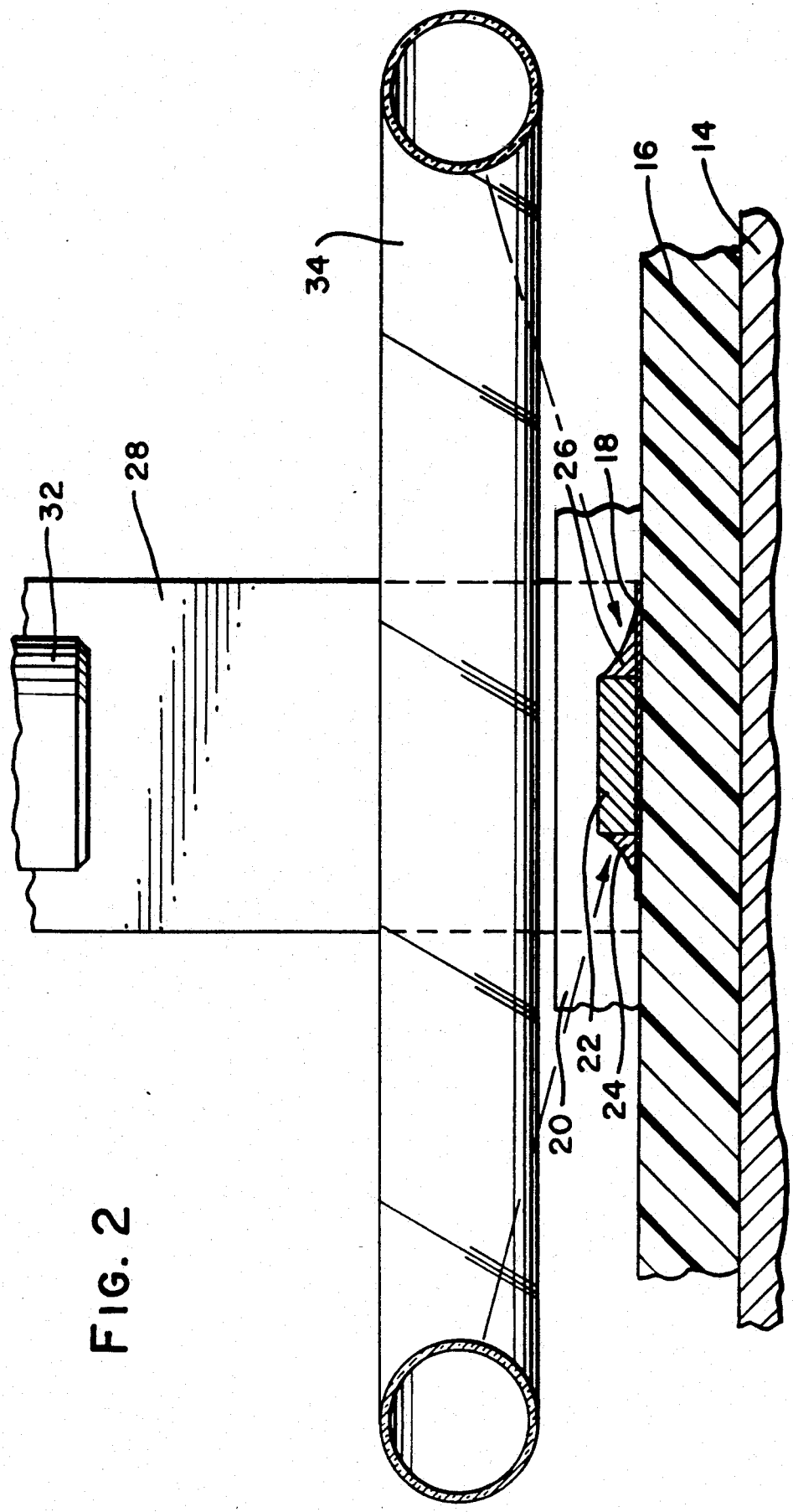
FIG. 2 is an enlarged section through the inspection station, showing the solder joint being inspected and a portion of the optical inspection system.

In FIG. 1, the optical inspection system of this invention is generally indicated at 10. The system comprises an optical portion, including lens 32 and lamp 34, and an electronic portion including digitizer-analyzer 38 and computer 42, connected by an optical-electronic transducer, such as video camera 30. The inspection takes place at an inspection station which includes table 12, which may be part of an assembly system. The top of the table represents the X and Y orthogonal coordinates, and the Z coordinate is normal thereto. Positioned on table 12 is platform 14, which is movable on X and Y coordinates, normal to the Z coordinate, to position a particular location on the inspection axis. The subject matter being inspected is the adequacy of the solder joint between leads on an electrical component and pads on the printed wiring board. Printed wiring board 16 is mounted on the platform 16 by means of a suitable fixture. It carries thereon a plurality of solder pads, one of which is seen at 18 in FIG. 2. In the usual processing, solder pad 18 has sufficient solder thereon prior to the soldering operation that, when a lead is placed thereon and heat is applied, the solder melts and fills the gap between the lead and the pad. In the present case, a portion of a component 20 is shown in FIG. 2. It has a rectangular lead 22 extending therefrom and positioned on pad 18. Previously to the positioning of the lead on the pad, suitable cleaning and fluxing have taken place to normally result in good solder attachment. Heater bars have been placed upon the lead 22 and heat applied so that solder has reflowed from the pad to wet and join both the pad and the lead. Fillets 24 and 26 are representative of good soldering. It is to be noted that the fillets are concave in the upward direction and outward from the lead. While the rectangular lead is shown, a round wire lead has similar fillets when properly soldered on a pad.

Stand 28 supports video camera 30 above the lead. The lens 32 of the video camera defines the axis at the center of the video field. The X-Y platform 14 moves the lead 22 onto the axis for video observation. Illumination is provided by a lamp which provides low angle, 15 to 17 degrees, diffuse illumination all around the area being inspected. Circular fluorescent lamp 34 is preferred. A high intensity, small diameter lamp is required. It provides light at a low angle with respect to the top of the printed wiring board 16 by being positioned as low as possible closely over the printed wiring board 16 as clearances permit. A specific example of a suitable light is a 3.5 inch diameter, 40 watt "Light Mite" circular high intensity fluorescent lamp. The large area diffused light fluorescent lamp distributes light intensity evenly over a large area thereby eliminating confusing shadows and specular reflections. The light source from the circular fluorescent lamp is at such a low angle with respect to the top of the board that light therefrom does not provide upward reflection from flat and horizontal surfaces. The angles illustrated in FIG. 2, 15 to 17 degrees, provide optimum illumination. It is to be noted, however, that the concave surf of fillets 24 and 26 reflect a substantial part of the incident light upwardly. The top surfaces of the lead 22 and of the printed wiring board are thus comparatively dark and the concave surfaces of the proper fillets are comparatively bright. Hence the features of interest are distinct from background and non-features and the edges of the lead are distinctly contrasted from the fillets.

The video camera 30 with its lens 32 is directed at the lead and convert that image of light and dark to a video signal. The video signal is present in line 36. A black and white camera is adequate because the image scene is a high contrast image without significant color. A color camera can be used to detect organic contamination or exposed copper. A video monitor can be connected to video signal line 36, but such is merely for observation and is not an essential part of the present inspection system. The video signal on line 36 is an analog signal, with line-by-line scan information interspersed therein. This analog information is difficult to process and interpret. Thus, it is fed to digitizer 38 where the image information is translated to digital signals. Furthermore, digitizer 38 includes an image analyzer to determine the quality of the solder joint. The analyzer accepts or rejects the solder joint on the basis of satisfying one rule, which requires fillet along a predetermined portion of the length of the lead. In commercial work, a 60 percent continuity of fillet is adequate. In high reliability work, a higher continuity is required. The absence of reflection from a significant length of the fillet indicates the inadequacy of fillet, and thus indicates the absence of a proper solder joint.

When the analysis of one particular lead connection has been completed, an output in quality control line 40 signals the adequacy or inadequacy of the inspected solder joint to control computer 42. The control computer 42 has an output signal line 44 by which the information as to the acceptability of the particular solder joint is recorded. It also provides an output signal in proceed line 46 which signals the X-Y controller 48 to move the X-Y platform to a new position wherein a new lead is on the inspection axis. Thus, the control computer 42 relates the quality decision to the particular solder joint and provides the go-ahead information. A continuous loop is formed, and when the X-Y controller has a new lead on the inspection axis, the optical signal is digitized, analyzed, and informs the control computer 42 that is ready to have its information recorded and proceed to the next solder joint. Such inspections are thus of individual leads and progress rapidly so that inspection rates are an order of magnitude faster than visual inspection rate. With a more complex inspection program, more than one soldered lead can be inspected at a time.

Figure 3:
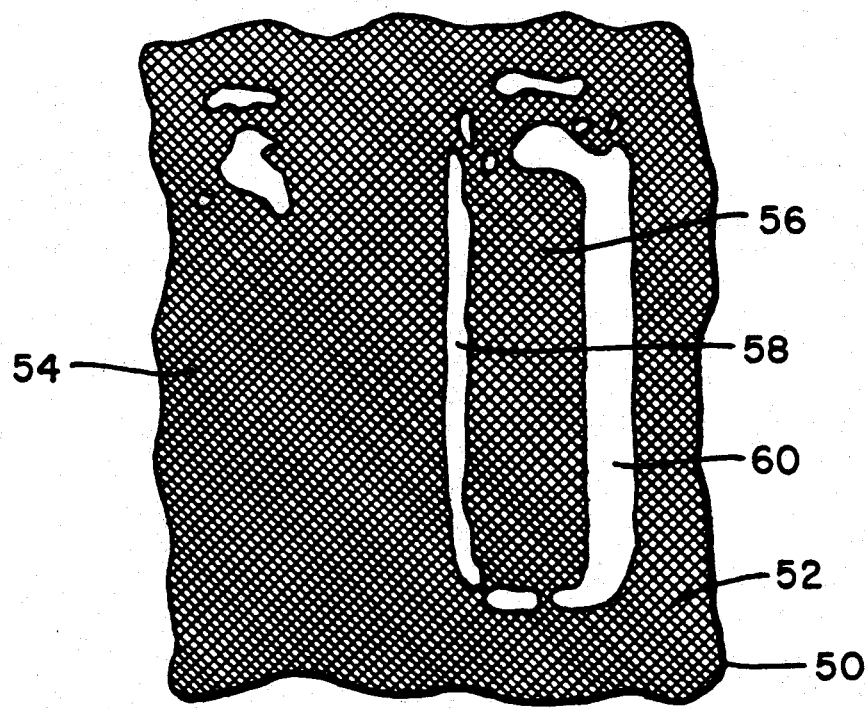
FIG. 3 is a plan view of two solder joints as seen by the inspection system with the lighting of this invention, showing an unsoldered joint and a soldered joint.

FIG. 3 is a plan view of first and second adjacent rectangular component leads soldered onto pads on a printed circuit board, illuminated in the manner described above and shown in FIGS. 1 and 2.

Figure 4:
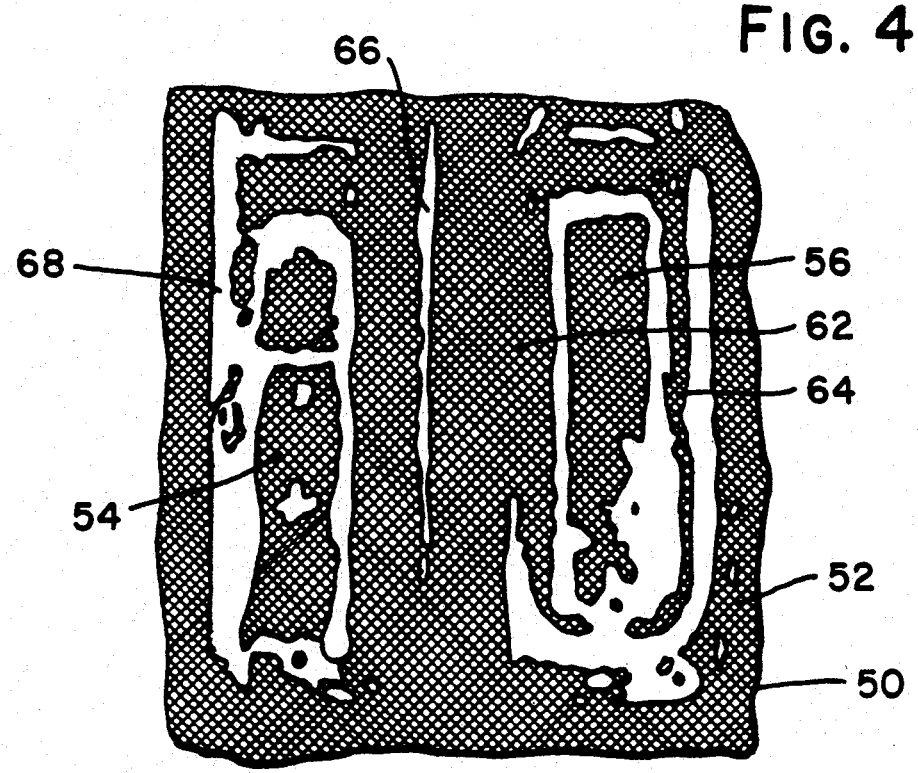
FIG. 4 is a plan view of the same two joints, illuminated at 45 degrees to the normal in accordance with modern visual inspection.

FIG. 4 is a plan view of the same two the component leads and solder condition, illuminated from an angle above 45 degrees to the top face of the printed wiring board in the conventional way. Two leads are shown in these figures, the leads being adjacent each other on the edge of a component package and being presumptively soldered to adjacent pads on the printed wiring board. This is illustrative of the camera view resulting from the two types of lighting. In the system described above, only one solder joint would be inspected at a time. The two leads thus represent successive inspection areas. The printed wiring board is shown at 50 in FIGS. 3 and 4, and its top surface 52 shows up as black on a high-contrast image because little light reflects therefrom with low angle lighting. The area 54 in FIGS. 3 and 4 is the top surface of the first lead. IN FIG. 3 with low angle lighting, it appears continuous with the background, which is represented by the top surface of the printed wiring board. The lead surface 54 is also shown in FIG. 4. Lead surface 56 is the top of the second lead in each of the images. The second lead with top surface 56 is properly soldered, and the concave surfaces of the fillet, such as shown at 24 and 26 in FIG. 2, reflect the diffuse low angle lighting upward to show bands 58 and 60. These are bright bands and are white in a high-contrast image system, as provided in the present invention.

These bright bands represent proper soldering and an adequate fillet. These areas should be compared with the dark bands 62 and 64, which are the solder fillets and show up as dark bands on the high angle lighted image of FIG. 4. If these dark bands are to be interpreted as proper solder joints, then they must be outlined by the bright band seen at the right of FIG. 4. These bright bands correspond to the edges of the fillet. The random white spots correspond to reflections from the pads. For example, in FIG. 4, light band 66 is a reflection from the top of the solder pad, and the light band 68 is also a reflection from the pad. The lead on the left is inadequately soldered, and this clearly shows up in FIG. 3 where little reflection is observed. There is no solder fillet to reflect the low angle lighting. Thus, the flat surfaces and square edges of the component lead and solder pad are not seen in FIG. 3, as they are in FIG. 4.

From this observation of the two leads, with the left one having an inadequate solder attachment and the right one having an adequate solder attachment, it is apparent that the differences in observed high-contrast image are insufficient with high angle light and sufficient with low angle light to permit computer analysis of the image produced when low angle illumination is employed. The diffused low angle lighting will reliably illuminate the concave fillets of the good solder joints while illuminating nothing else.

The high angle lighting will not reliably illuminate the concave fillets, sometimes introducing confusing shadows and specular glares into the image. It also illuminates the features of the bad or missing fillets. The results are complex and confusing images without differentiating the good and bad features.

On the contrary, the low angle diffused lighting brightens the features of the good fillets (i.e. concave surfaces) while darkening the features of bad fillets or non-features. The effects are wider dynamic range of electronic signals between bad and good features, thereby facilitating discriminating the good from the bad joints. The electronic analog television images are digitized, and the shape thereof and completeness of the bands is analyzed to determine compliance to a rule which requires a continuous fillet along a predetermined proportion of the total potential fillet length. When the standard has been met, a completion signal and an acceptance signal are emitted in line 40 to the control computer where the acceptance of that particular solder joint is recorded and the X-Y controller is instructed to move another solder joint onto the inspection axis. In this way, rapid, automatic, reliable inspection is achieved.

This invention has been described in its presently contemplated best mode, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. An optical inspection system comprising:
   positioning means for the locating of a soldering pad upon which lies a component lead which has been purportedly soldered thereon by concave fillets;
   an optical-electronic transducer defining an inspection axis, said optical-electronic transducer being positioned to receive an optical image along said axis, said optical-electronic transducer producing an electronic image signal;
   a non-polarized high intensity small diameter circular diffused fluorescent single-lamp light source positioned with respect to said positioning means and said axis, said single light source directing light toward said positioning means at an angle greater than 45 degrees with respect to said axis so that light from said light source is distributed evenly over a large area so as to eliminate shadows and specular reflections and said light strikes the pad at a low angle with respect to the pad so that top surfaces of the lead and the printed wiring board are comparatively dark relative to the light reflected from surfaces of said concave fillets, so that features of interest are distinct from back-ground and non-features; and
   means for digitizing the electronic image signal and means for analyzing the digitized image signal to evaluate the adequacy of the amount of fillet in the solder joint between the pad and the component lead by analyzing bands of said image signal to determine compliance to a rule which requires a continuous fillet along a predetermined portion of total potential fillet length.

2. The system of claim 1 wherein said optical-electronic transducer is a television camera.

3. The system of claim 2 wherein said television camera is positioned with its optical axis on said axis.

4. The system of claim 1 wherein said positioning means is a positioning table and said means for analyzing the digital image is connected to said positioning table so that when the analysis of a solder joint is complete, the positioning table moves to a position where a new pad and its component lead are on said axis.

5. The system of claim 4 wherein said positioning table is an X-Y table and said means for analyzing and evaluation the digitized image is connected to a control computer, said control computer being for recording the results of the analysis and for signaling movement of the X-Y table to a new position.

6. The system of claim 4 wherein said optical-electronic transducer is a television camera.

7. The system of claim 6 wherein said television camera is positioned with its optical axis on said axis.

8. An optical inspection system for solder joints comprising:
   a support for a printed wiring board having a surface with pads thereon and having components mounted on the printed wiring board and having component leads presumptively soldered to the pads on the printed wiring board with concave fillets, an axis substantially perpendicular to the pads, said support being a positioning table for holding thereon a printed wiring board with a plurality of pads, each having a component lead purportedly soldered thereto with a concave fillet;
   a television camera positioned substantially on said axis, said television camera being for optically observing solder pads and leads substantially on said axis to create an optical image thereof and converting the optical image to electronic image information;
   means for illuminating said support at said axis, said means for illumination comprising a single lamp high intensity, non-polarized diffuse low angle illumination about 15 degrees above the surface substantially around said axis with the angle being sufficiently low so that direct light reflection from the surface of the printed wiring board is not directed along said inspection axis and is distributed evenly over a large area so as to eliminate shadows and specular reflections;

means for digitizing the electronic image information;

means for analyzing the digitized image information for indicating the presence of solder fillets around the component lead to evaluate the adequacy of the solder joint between the component lead and the pad on the printed wiring board to produce a solder adequacy signal by analyzing bands of said digitized image to determine compliance to a rule which requires a continuous fillet along a predetermined portion of total potential fillet length;

control computer means for recording the solder adequacy signal; and positioning table drive means connected to receive a signal from said control computer means for repositioning said table and the printed wiring board supported thereon to place another printed wiring board in position under said television camera for inspection.

9. The system of claim 8 wherein said means for illuminating is a circular fluorescent light positioned closely above said support to provide low angle about 15 degrees above the surface diffuse illumination substantially all the way around said axis.

10. The system of claim 9 wherein said support is a positioning table for holding thereon a printed wiring board with a plurality of pads, each having a component lead purportedly soldered thereto and upon receipt of a solder adequacy signal, said control computer signals said positioning table to move to place another pad on said axis.

11. The method of inspecting solder joints wherein a printed wiring board has a pad thereon and has a component lead purportedly soldered thereon comprising the steps of:

illuminating the pad with low about 15 degrees angle high intensity non-polarized diffuse light from a single lamp source positioned as low as possible closely over the printed wiring board as clearances permit and which light is distributed evenly over a large area so as to eliminate shadows and specular reflections;

optically imaging the pad;

transducing the optical image to digitize image information;

comparing the digitized information with digitized patterns and logic rules which determine the proportional length of concave fillet corresponding to an adequate solder joint wherein said logic rules analyze bands of said digitized information to determine compliance to a rule which requires a continuous fillet along a predetermined portion of total potential fillet length; and emitting a signal indicating the acceptance or rejection of the inspected solder joint.

12. The method of claim 11 further including repositioning the printed wiring board after the solder acceptance or rejection signal has been produced.

13. The method of claim 11 further including the preliminary step of positioning a printed wiring board having a plurality of pads thereon and having a corresponding plurality of component leads thereon; and repositioning the printed board to place a new pad for optical inspection when a solder acceptance or rejection signal is produced so as to automatically advance to any new inspection position.

14. The method of optically inspecting a solder joint comprising the steps of:

positioning a printed wiring board having a pad thereon with a lead on the pad purportedly soldered to the pad by means of concave solder fillets between the pad and the lead on an axis;

positioning a circular diffused fluorescent single lamp light source close to said solder joint to provide low angle non-polarized light aproximately 15 degrees onto the pad so that reflection from the printed wiring board, pad and lead do not directly reflect on the axis and reflection from the solder fillets reflects on the axis;

transducing the optical image to digitized optical information;

analyzing bands of said image to determine compliance to a rule which requires a continuous fillet along a predetermined portion of total potential fillet length in order to determine the adequacy of the solder fillet;

issuing a signal corresponding to the adequacy of presence of solder fillet to indicate adequate soldering and signaling repositioning of the printed wiring board to place another pad on the axis.

* * * * *